(12) United States Patent
Gittard et al.

(10) Patent No.: US 9,707,070 B2
(45) Date of Patent: Jul. 18, 2017

(54) MIGRATION-RESISTANT GASTROINTESTINAL BARRIER

(71) Applicant: Cook Medical Technologies LLC, Bloomington, IN (US)

(72) Inventors: Shaun D. Gittard, Winston-Salem, NC (US); Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/789,574

(22) Filed: Jul. 1, 2015

(65) Prior Publication Data

US 2016/0000549 A1 Jan. 7, 2016

Related U.S. Application Data

(60) Provisional application No. 62/021,426, filed on Jul. 7, 2014.

(51) Int. Cl.
*A61F 2/38* (2006.01)
*A61F 2/00* (2006.01)
(Continued)

(52) U.S. Cl.
CPC .............. *A61F 2/0077* (2013.01); *A61F 2/04* (2013.01); *A61F 2/844* (2013.01); *A61F 2/848* (2013.01); *A61F 2/90* (2013.01); *A61L 31/022* (2013.01); *A61L 31/04* (2013.01); *A61L 31/12* (2013.01); *A61L 31/14* (2013.01); *A61L 31/146* (2013.01); *A61F 2002/0086* (2013.01); *A61F 2002/044* (2013.01); *A61F 2002/045* (2013.01);
(Continued)

(58) Field of Classification Search
CPC .......... A61F 2/0077; A61F 2/04; A61F 2/844; A61F 2/848; A61F 2/90
USPC ....... 623/1.24, 1.26, 2.14, 2.18, 1.38, 23.64, 623/23.65, 23.68, 23.7, 23.76, 23.74, 623/23.72; 604/8
See application file for complete search history.

(56) References Cited

U.S. PATENT DOCUMENTS 5,736,470 A * 4/1998 Schneberger .............. C09J 7/04
156/295
5,928,972 A * 7/1999 Mashiko ............. A61F 13/0276
442/286
(Continued)

FOREIGN PATENT DOCUMENTS

WO WO 00/12027 A1 3/2000

OTHER PUBLICATIONS

International Search Report completed Sep. 28, 2015 for International Application No. PCT/US2015/038744.
(Continued)

*Primary Examiner* — Alvin Stewart
(74) *Attorney, Agent, or Firm* — Brinks Gilson & Lione

(57) ABSTRACT

A prosthesis and a method for securing a prosthesis at a treatment site are provided. The prosthesis includes a material portion. The material portion includes a liquid-impermeable material layer, a porous material layer having a pore size adapted for promoting tissue ingrowth, and an adhesive portion provided on the porous material layer adapted to secure the material portion to a site for at least 24 hours following implantation of the prosthesis at the site. In some embodiments, the prosthesis further includes a body.

19 Claims, 6 Drawing Sheets

(51) Int. Cl.
 *A61F 2/04* (2013.01)
 *A61F 2/844* (2013.01)
 *A61F 2/848* (2013.01)
 *A61F 2/90* (2013.01)
 *A61L 31/02* (2006.01)
 *A61L 31/04* (2006.01)
 *A61L 31/12* (2006.01)
 *A61L 31/14* (2006.01)

(52) U.S. Cl.
 CPC . *A61F 2220/005* (2013.01); *A61F 2220/0008* (2013.01); *A61F 2250/0024* (2013.01); *A61F 2250/0025* (2013.01)

(56) References Cited

U.S. PATENT DOCUMENTS

| | | |
|---|---|---|
| 6,312,457 B1 | 11/2001 | DiMatteo et al. |
| 2002/0049503 A1 | 4/2002 | Milbocker |
| 2002/0165601 A1* | 11/2002 | Clerc .................. A61F 2/07 623/1.13 |
| 2004/0107004 A1* | 6/2004 | Levine ............... A61B 17/0401 623/23.64 |
| 2006/0079957 A1 | 4/2006 | Chin et al. |
| 2010/0191167 A1* | 7/2010 | Laufer ................. A61F 5/0076 604/8 |
| 2011/0009801 A1* | 1/2011 | Blaeser ............... A61B 17/064 604/8 |
| 2011/0087146 A1* | 4/2011 | Ryan .................... A61F 2/04 604/8 |
| 2012/0059294 A1* | 3/2012 | Schubert ............. A61F 13/0203 601/46 |
| 2012/0116285 A1* | 5/2012 | Duggirala ............ A61F 5/0079 604/8 |
| 2013/0030351 A1* | 1/2013 | Belhe .................. A61F 5/0076 604/9 |
| 2013/0116645 A1* | 5/2013 | Corley ................ A61L 15/26 604/369 |
| 2014/0114230 A1* | 4/2014 | Baker ................. A61F 2/04 604/8 |
| 2014/0257164 A1* | 9/2014 | Gittard ................ A61F 5/0089 604/8 |
| 2015/0045876 A1* | 2/2015 | Clerc .................. A61F 2/82 623/1.38 |
| 2015/0283362 A1* | 10/2015 | Shelton ............... A61M 27/002 604/8 |

OTHER PUBLICATIONS

Written Opinion completed Sep. 28, 2015 for International Application No. PCT/US2015/038744.

* cited by examiner

MIGRATION-RESISTANT GASTROINTESTINAL BARRIER

RELATED APPLICATIONS

This application claims the benefit of U.S. Provisional Application No. 62/021,426, filed Jul. 7, 2014, which is incorporated by reference herein in its entirety.

FIELD OF THE INVENTION

The present invention relates to medical devices and in particular to a migration-resistant gastrointestinal barrier.

BACKGROUND OF THE INVENTION

Numerous gastrointestinal diseases can be treated by implantation of medical devices in the gastrointestinal (GI) tract. These diseases include Type II diabetes, obesity, GERD, anastomotic leaks, fistulas and ulcerative colitis. A wide variety of devices exist to treat these diseases including stents, sleeves and valves. One challenge in attaching treatment devices to the GI tract is migration. The causes of migration are multi-fold. First, the mucosal layer of the GI tract frequently soughs off and renews, limiting the ability of attaching devices long-term in the duodenum via attachment to the mucosa. Second, peristaltic motion in the GI tract makes implants prone to migration. In addition, digestive enzymes in the GI tract can degrade many implanted materials.

What is needed is a prosthesis that provides for both short-term and long term anchoring of a barrier in the GI tract.

BRIEF SUMMARY

Accordingly, it is an object of the present invention to provide a device and a method having features that resolve or improve on the above-described drawbacks.

A migration resistant prosthesis is provided. The prosthesis includes a material portion. The material portion includes a liquid-impermeable material layer, a porous material layer having a pore size adapted for promoting tissue ingrowth, and an adhesive portion provided on the porous material layer adapted to secure the material portion to a site for at least 24 hours following implantation of the prosthesis at the site. In some embodiments, the prosthesis further includes a body.

In another aspect, a method of securing a prosthesis at a treatment site in a bodily lumen to inhibit migration of the prosthesis is provided. The method includes positioning a material portion of a prosthesis within the bodily lumen, the material portion including a liquid-impermeable material layer, a porous material layer having a pore size adapted for promoting tissue ingrowth. The method further includes contacting the porous material layer with the bodily lumen and adhering the portion of the material portion to the bodily lumen with an adhesive portion on the porous material layer so that the adhesive portion secures the porous material layer to the bodily lumen for at least 24 hours following implantation of the prosthesis at the site and the porous material layer is between the bodily lumen and the liquid-impermeable layer.

DETAILED DESCRIPTION

Figure 1:
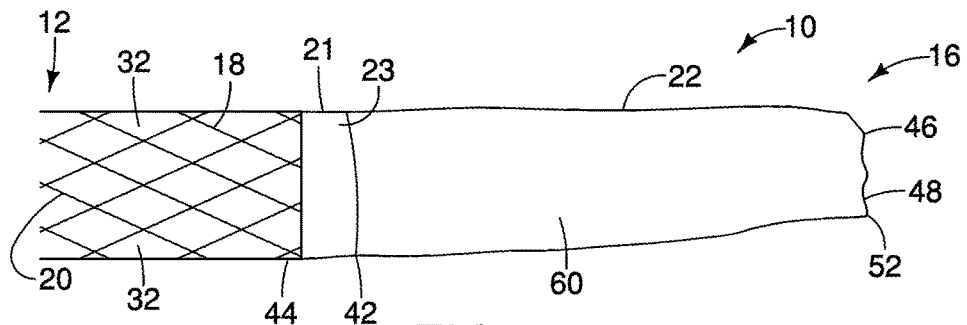
FIG. 1 is a side view of a prosthesis in accordance with an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the gastrointestinal barrier to a patient. Hence the term "distal" means the portion of the gastrointestinal barrier that is farthest from the physician and the term "proximal" means the portion of the gastrointestinal barrier that is nearest to the physician.

The present invention relates to medical devices, and in particular to prosthetic barrier devices for implantation in a body lumen such as the gastrointestinal tract. As used herein, the term "implantable" refers to an ability of a medical device to be positioned at a location within a body, such as within a body lumen, either temporarily, semi-permanently, or permanently. Permanent fixation of the device in a particular position is not required. Furthermore, the terms "implantation" and "implanted" refer to the positioning of a medical device at a location within a body, such as within a body lumen.

Figure 4:
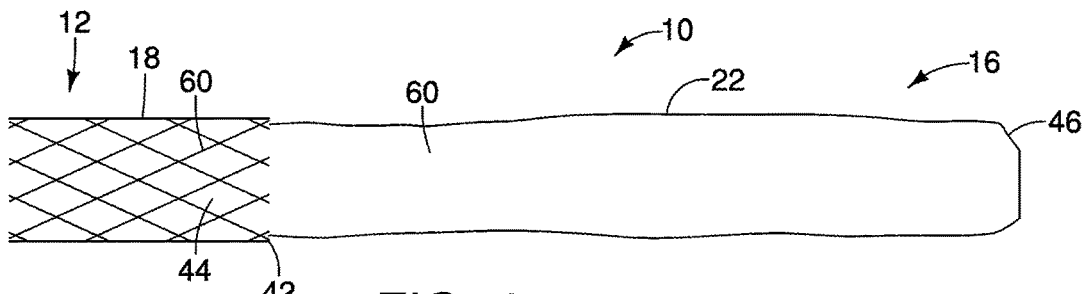
FIG. 4 is a side view of a prosthesis in accordance with an embodiment of the present invention.
Figure 2:
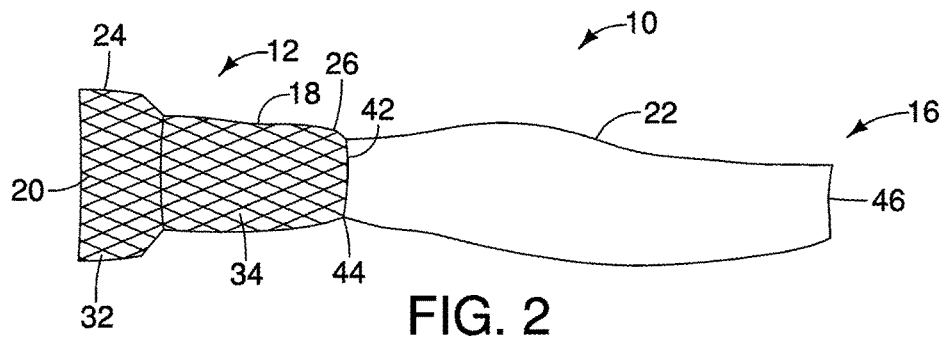
FIG. 2 is a side view of a prosthesis in accordance with an embodiment of the present invention.

FIG. 1 illustrates a prosthesis 10 in accordance with an embodiment of the present invention. The prosthesis 10 has a proximal portion 12 and a distal portion 16. The proximal portion 12 includes a tubular body 18 having a lumen 20 extending therethrough. The distal portion 16 includes a material portion 22 extending distally from the body 18. In some embodiments the material portion 22 may be provided as a sleeve with a lumen therethrough and in other embodiments the material portion may be provided as a patch without a lumen. In some embodiments, the body 18 may be an expandable stent such as a self-expandable stent or a balloon expandable stent. Non-limiting examples of expandable stents include the Z-Stent® and the EVOLUTION® stent (Cook Medical Incorporated, Bloomington, Ind.). The body 18 provides a force extending radially outward against a wall of a patient's lumen to facilitate holding the prosthesis in position at a delivery site within the patient's lumen. In some embodiments, the body 18 may include a proximal end portion 24 having an expanded outer diameter as shown in FIG. 2. In some embodiments, a distal end portion 26 of the body 18 may include an expanded outer diameter. In some embodiments, the body 18 may be a substantially straight tubular shape as shown in FIGS. 1 and 4.

Figure 3:
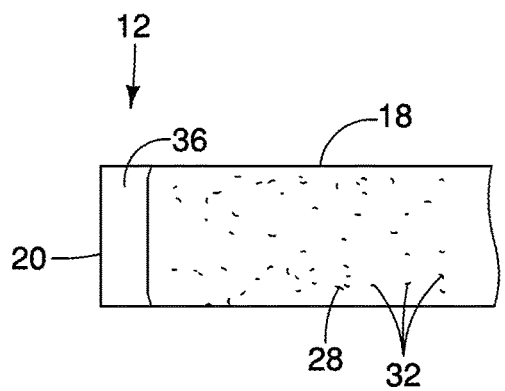
FIG. 3 is a side view of a body of the prosthesis in accordance with an embodiment of the present invention.

In some embodiments, the body 18 may include a porous material portion 28 connected to the body 18 as shown in FIG. 3. The porous material portion 28 is adapted to expand and compress with the radial force of the body 18. In some embodiments, the body 18 may include the porous material portion 28 and/or at least a portion of the body 18 itself may comprise the porous material 28 to allow for tissue ingrowth into openings 32 at the final delivery site to affix the body 18 to the patient's luminal wall. The porous material 28 may completely cover the body 18, partially cover the body 18 or the body 18 may be uncovered with the openings 32 extending through the body comprising the porous material portion 28. The porous material portion 28 may be positioned on an exterior surface 36 of the body 18 as shown in FIG. 3. In some embodiments, the porous material portion 28 may be extruded over the body 18. Alternatively, the porous material portion 28 may be woven together with the body 18 or positioned on an interior surface of the body 18. In some embodiments, the body 18 may include a coating 34 on a portion of the body 18 that is liquid impermeable so that liquid and nutrients flowing from the proximal portion 12 to the distal portion 16 do not pass through the coated portion 34 of the body 18. The body 18 with the coating 34 includes the porous portion 28 so that tissue may grow into the porous portion 28 to hold the prosthesis 10 in position at the treatment site. The porous portion 28 may be over the coating 34 or proximal to the coating 34. The porous portion 28 is adapted to allow tissue ingrowth the affix the prosthesis 10 to the treatment site for longer term anchoring in addition to and after a short term anchoring system has been used as described in more detail below.

In some embodiments, the body 18 of the prosthesis 10 may be woven or folded in a wave shape. Non-limiting examples of materials that form the proximal portion 12 include metals, such as nitinol, stainless steel and platinol, polymers such as polyester, nylon and polyolefin, or a composite such as fiberglass. Other materials that form the body 18 may also be used.

A proximal portion 23 of the material portion 22 of the distal portion 16 of the prosthesis 10 is connected to a distal portion 21 of the body 18 as shown in FIG. 1. In some embodiments, the proximal portion 23 of the material portion 22 may overlap the distal portion of the body 21 as shown in FIGS. 1 and 4. As shown in FIG. 1, the proximal portion 23 of the material portion 22 may be positioned over the distal portion 21 of the body 18. In some embodiments, the distal portion 21 of the body 18 may be positioned over the proximal portion 23 of the material portion 22 as shown in FIG. 4. A distal end 42 of the body 18 may be connected to a proximal end 44 of the material portion 22 as shown in FIG. 2 in some embodiments. The connection between the body 18 and the material portion 22 may be liquid impermeable so that fluid flowing through the lumen 20 of the body flows into a lumen 46 of the material portion 22. The material portion 22 may be connected to the body 18 by any method known to one skilled in the art. By way of non-limiting example, the material portion 22 may be connected to the body 18 by sewing, gluing, melting, fusing, welding, and the like.

The material portion 22 may be formed of a liquid impermeable, thin, flexible material so that the liquid transported through the material portion 22 does not exit through a wall of the material portion 22. The material portion 22 may be self-closing so that walls of the material portion contact each other and impede fluid flow through the material portion 22 toward the body 18, but allow fluid flow from the body 18 through the material portion 22 and out an opening 48 at a distal end 52 of the lumen 46 of the material portion 22. For example, the material portion 22 may be self-closing when the prosthesis 10 is positioned in the lower esophageal sphincter (LES). In some embodiments, the material portion 22 may remain open so that food and liquid can pass through and out the opening 48, for example, when the prosthesis 10 is positioned in the duodenum.

In some embodiments, the material portion 22 may be thin-walled with a thickness ranging from about 0.01 mm to about 0.5 mm. In some embodiments, the material portion 22 may be formed from a plurality of layers and may include porous and/or nonporous regions. By way of non-limiting example, the material portion 22 may be formed from elastomers, thermoplastics, fluoropolymers, polymer weaves, non-woven polymers, biodegradable polymers, biologic materials and combinations thereof. In some embodiments, the material portion 22 may be made from polyolefin, nylon, nitrile, latex, polyisoprene, polyesters (PLA, PGA, PET, PCL, etc.) fluoropolymers (PTFE), biological materials (small intestine submucosa) and combinations thereof. In some embodiments, the material portion 22 may be solid, woven (i.e. DACRON, GORE-TEX, KEVLAR, DYNEEMA, etc.) or non-woven (i.e. TYVEK). Combinations of materials may be used on the entire material portion 22 or on portions thereof.

The prosthesis 10 also includes an adhesive portion 60 that is adapted to contact tissue at the treatment site to hold the prosthesis 10 in position for at least a short period of time. Typically, migration of an implanted prosthesis occurs within 24 hours of implantation. The adhesive portion 60 is adapted to inhibit the initial migration by securing at least a portion of the material portion 22 to the tissue. In some embodiments, the adhesive portion 60 is adapted to hold the prosthesis 10 in position at the treatment site for at least about 24 hours, 30 hours, 36 hours, 42 hours, 48 hours, 72 hours, 96 hours, 120 hours, 144 hours, or 168 hours following implantation of the prosthesis at the site. The adhesive portion 60 may be used to inhibit migration of the prosthesis 10 until tissue ingrowth into the porous material 28 is sufficient to hold the prosthesis 10 in position at the treatment site.

Figure 5:
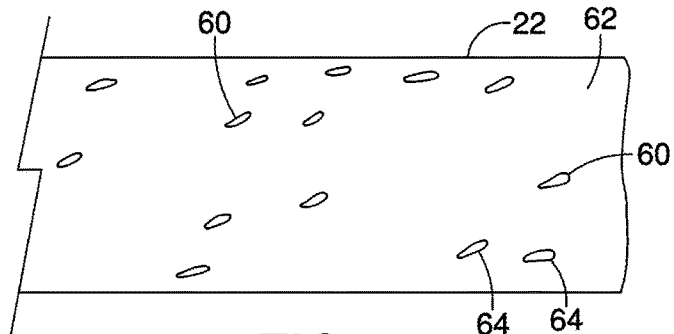
FIG. 5 is a partial view of a material portion of the prosthesis in accordance with an embodiment of the present invention.
Figure 6:
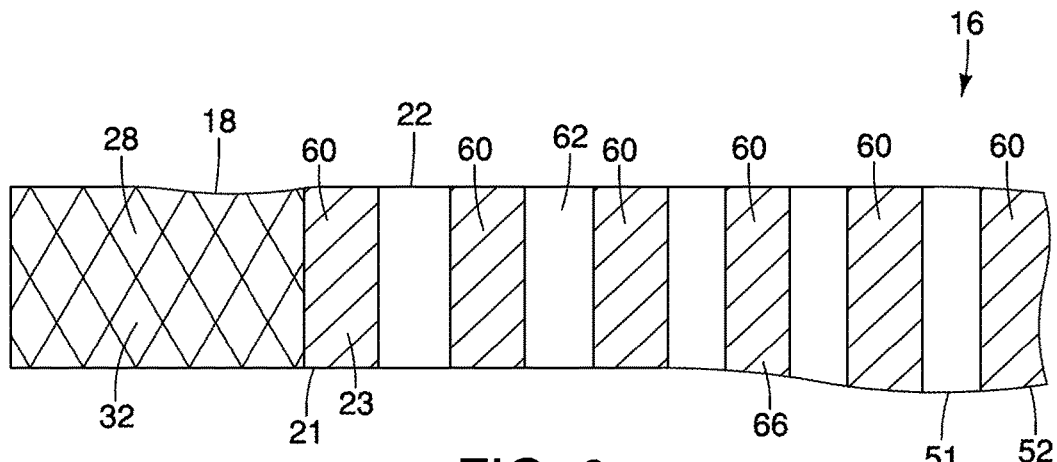
FIG. 6 is a side view of a prosthesis in accordance with an embodiment of the present invention.
Figure 7:
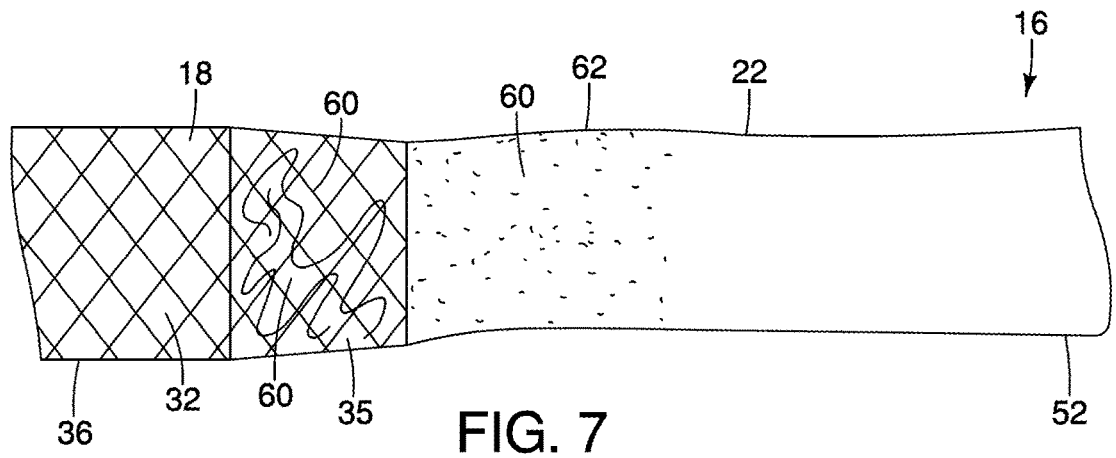
FIG. 7 is a side view of a prosthesis in accordance with an embodiment of the present invention.

In some embodiments, the adhesive portion 60 may be located on an outer surface 62 of the material portion 22. In some embodiments, the outer surface 62 of the material portion 22 may be a porous outer surface 62 so that the adhesive portion 60 may flow through pore openings 64 in the porous outer surface 62 when contacting a fluid within the body lumen of the patient to form a bond between the outer surface 63 of the material portion 22 and the tissue. In some embodiments, the adhesive portion may be distributed randomly over at least a portion of the outer surface 62 as shown in FIGS. 5 and 7. In some embodiments, the adhesive portion 60 may be applied to the outer surface 62 of the material portion 22 in a pattern as shown in FIG. 6. For example, when the prosthesis 10 is positioned within the duodenum, the adhesive portion 62 may be included on the distal end 52 of the material portion 22 to facilitate holding the material portion 22 open. The material portion 22 may also have a porous outer surface 62 on the distal end 52 having a plurality of pores 64 to facilitate tissue ingrowth for long term implantation. In some embodiments, the pore size may be between about 20 and 1000 microns. In some embodiments, the pore size may be between about 50 and 300 microns. In some embodiments, the adhesive portion 60 may extend from the proximal portion 23 of the material portion 22 to a distal portion 51 of the material portion 22. In other embodiments, the adhesive portion 60 may extend over the proximal portion 23 of the material portion 22 with the distal end 52 of the material portion 22 unadhered to tissue and free to close on itself, for example for when the prosthesis 10 is positioned in the LES.

Figures 9, 10:
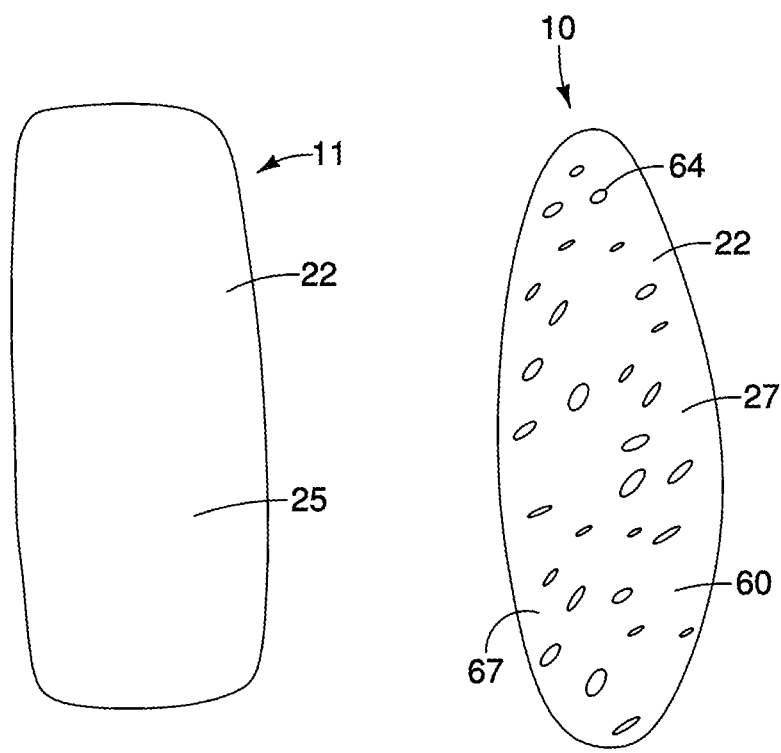
FIG. 9 is a first side of a prosthesis in accordance with an embodiment of the present invention.
FIG. 10 is second side of a prosthesis in accordance with an embodiment of the present invention.
Figure 11:
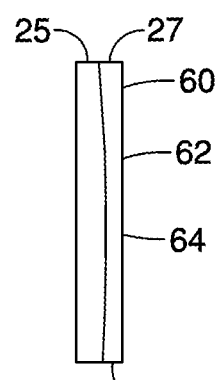
FIG. 11 is a section view through the embodiment shown in FIG. 9.
Figure 14:
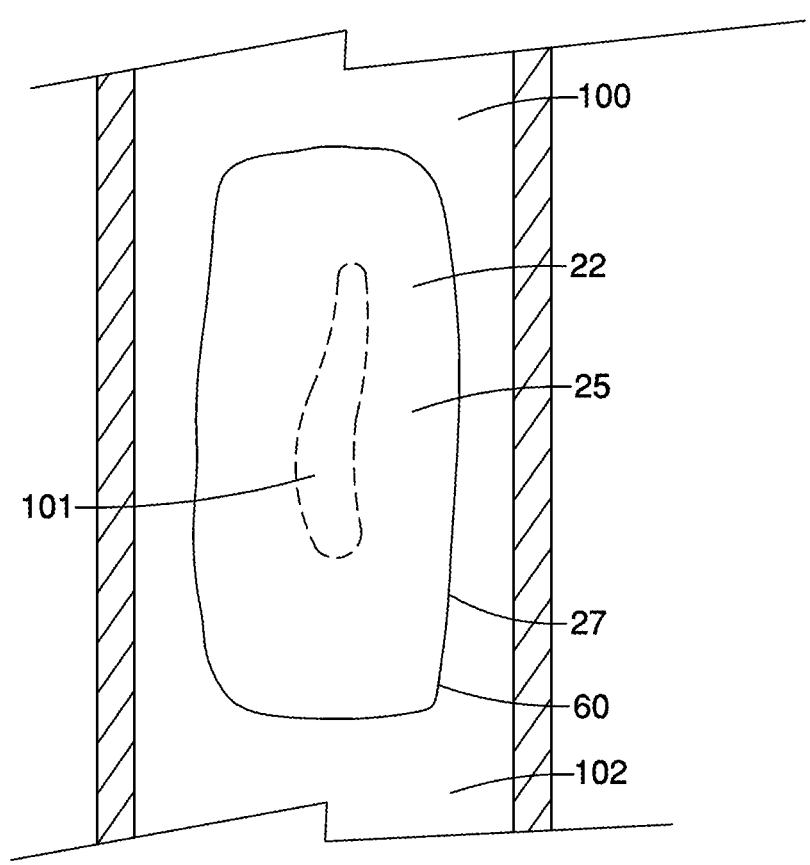
FIG. 14 illustrates an embodiment of a prosthesis positioned in a bodily lumen.

As shown in FIGS. 9-11, the material portion 22 may be provided as a patch of material without a body as described above. The material portion 22 of any of the embodiments described herein may include a liquid impermeable layer 25 and a porous layer 27 including a plurality of pores 64 to facilitate tissue ingrowth. The material portion 22 may be any shape suitable to fit within a body lumen and maybe configured to be cut to size depending on the size and shape of the lumen into which the material portion 22 is to be implanted. By way of non-limiting example, the material portion 22 may be used to cover an ulcerated tissue and the material portion 22 may be sized and shaped to extend beyond the ulcerated tissue and yet fit with in the bodily lumen. Similar to the embodiments described above, the material portion 22 includes an adhesive portion 60 to adhere the prosthesis 10 to the bodily lumen. The adhesive portion 60 may be provided on the porous layer 27 to adhere the prosthesis 10 to the site until tissue ingrowth secures the prosthesis 10 in position. In some embodiments, the adhesive portion 60 may be provided on a periphery 67 of the material portion 22 to provide a liquid impermeable barrier over the site. In some embodiments, the adhesive portion 60 may be provided in a pattern or randomly on the material portion 22. FIG. 11 illustrates a sectional view through the material portion 22 showing the liquid-impermeable layer 25 and the porous layer 27. FIG. 14 illustrates the material portion 22 positioned within a bodily lumen 100 and covering an ulcerated portion 101 of the bodily lumen 100. The porous layer 27 and the adhesive portion 60 are positioned against a lumen wall 102 and the liquid-impermeable layer 27 is exposed to the bodily lumen 100.

Figure 8:
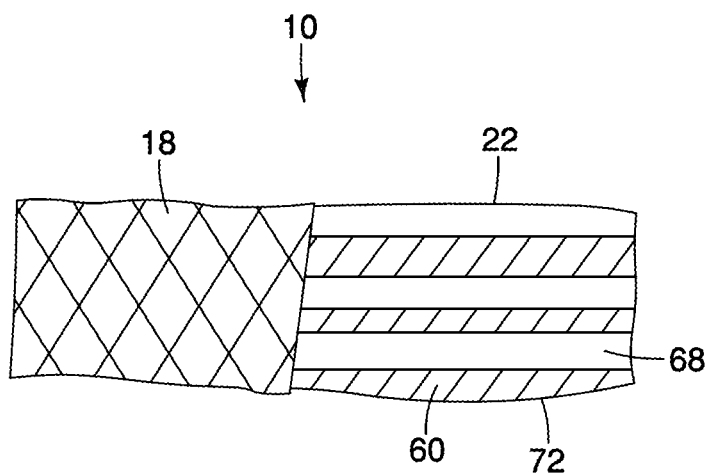
FIG. 8 is a side view of a prosthesis in accordance with an embodiment of the present invention.

In some embodiments, the adhesive portion 60 may also be provided on at least a portion of an outer surface 35 of the body 18. By way of non-limiting example, the adhesive portion 60 may be provided on the distal portion 21 of the body 18 to hold the body 18 in position in addition to the radially outward force provided by the body 18. In some embodiments, the adhesive portion 60 may be provided in bands 66 circumferentially surrounding the material portion 22 with spaces 68 between the bands 66 without the adhesive portion. In other embodiments, the adhesive portion may be provided in longitudinal bands 72 of the material portion 22 as shown in FIG. 8.

Exemplary adhesives for the adhesive portion 60 include but are not limited to carbomers, polycarbophil, cyanoacrylates, mussel adhesive protein derivatives, polyacrylic acid, polyethylene glycol, polyvinylpyrrolidone, epoxies, thermoset adhesives, UV adhesives, redux adhesives, natural adhesives (mucilages, lignin glue, fibrin glue and casein glue) and combinations thereof. The adhesive portion 60 may be applied to the prosthesis 10 by spraying dipping, brushing, rolling, and the like.

Figure 12:
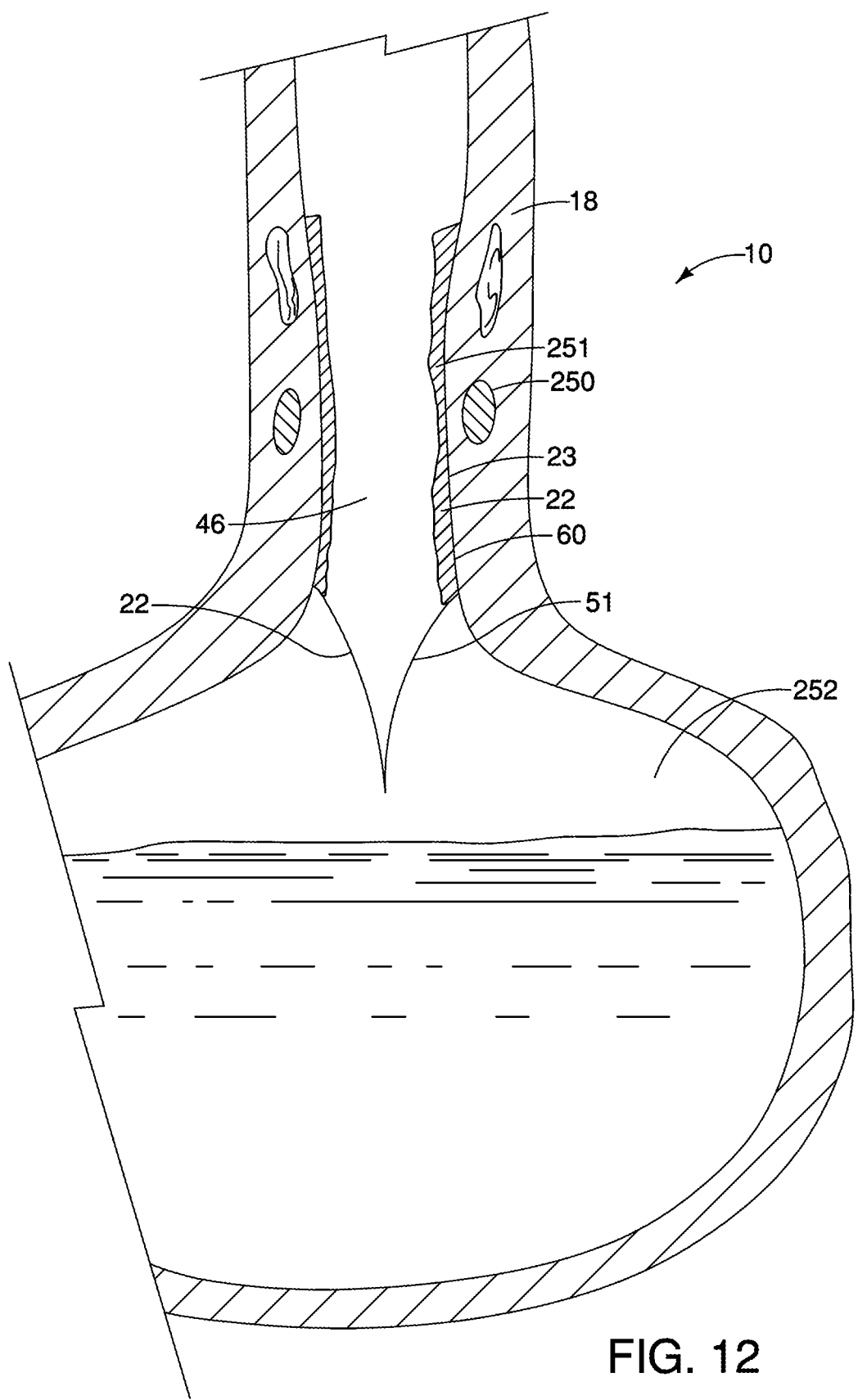
FIG. 12 illustrates an embodiment of a prosthesis positioned within the lower esophageal sphincter.
Figure 13:
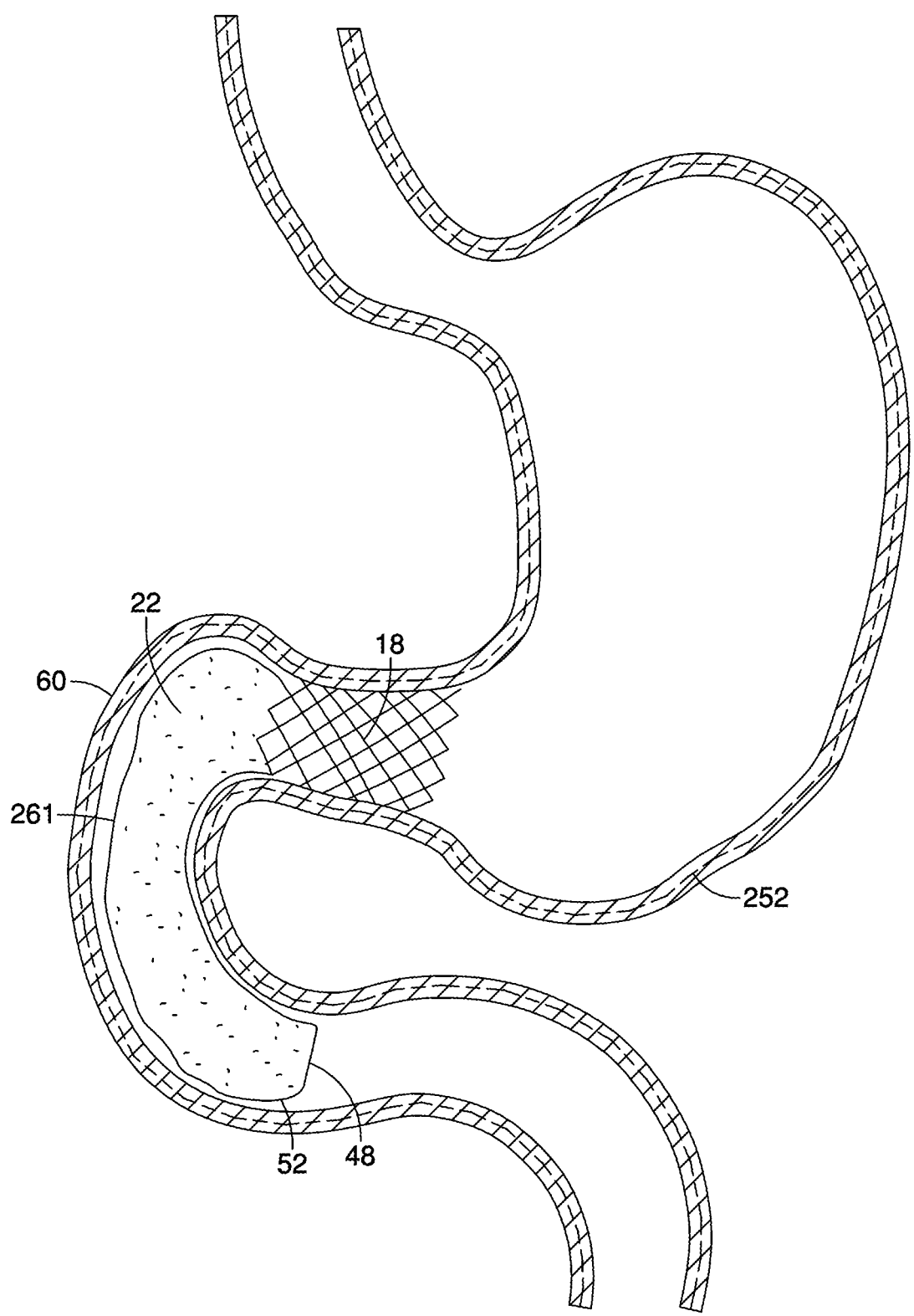
FIG. 13 illustrates an embodiment of a prosthesis positioned with in the duodenum.

As shown in FIG. 12, the prosthesis 10 may be positioned in the lower esophageal sphincter 250. The proximal portion 12 of the body 18 may be positioned proximal to the esophageal sphincter 250. The material portion 22 of the prosthesis 10 may be positioned so that the proximal portion 23 of the material portion 22 is anchored to the wall of the esophagus 251 with the adhesive portion 60. The distal portion 51 of the material portion 22 may extend into the stomach 252. As shown in FIG. 13, the prosthesis 10 may be positioned in the duodenum 261. As discussed above, the material portion 22 may be anchored to the wall of the duodenum 261 with the adhesive portion 60 along the length of the material portion 22 to that the distal end 52 of the material portion 22 remains open. The prosthesis 10 may be delivered to the position in the esophageal sphincter or the duodenum in a collapsed configuration using a delivery device known to one skilled in the art such as a delivery catheter. Once the prosthesis 10 is in position within the lumen of the patient, the adhesive portion 60 may be used to adhere at least a portion of the body 18 and or the material portion 22 to the luminal wall. The adhesive portion 60 may be activatable by contact with the bodily fluids, by light activation chemical activation or the like. Other positions within patient's body lumens are also possible for positioning the prosthesis 10 therein.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A migration resistant prosthesis, the prosthesis comprising:
    a material portion, the material portion comprising:
        a liquid-impermeable material layer having a proximal opening, a distal opening and a wall extending between the proximal and distal openings, the wall being free from fluid flow through the wall between the proximal opening and the distal opening;
        a porous material layer on an outer surface of the material portion, the porous material layer having a pore size adapted for promoting tissue ingrowth; and
        an adhesive portion provided on the porous material layer adapted to secure the material portion to a site for at least 24 hours following implantation of the prosthesis at the site.

2. The migration resistant prosthesis according to claim 1, further comprising a body having a proximal portion, a distal portion and a lumen extending therethrough, at least a portion of the body providing a force adapted to expand the body radially outward in a final position of the prosthesis, the body further comprising a porous portion adapted for tissue ingrowth, the material portion operably connected to the body and extending distally from the body.

3. The prosthesis according to claim 2, wherein the body comprises a metal, a polymer or a composite.

4. The prosthesis according to claim 2, wherein the porous portion covers a portion of the body.

5. The prosthesis according to claim 2, wherein a proximal end of the material portion is connected to a distal end of the body.

6. The prosthesis according to claim 1, wherein the material portion comprises a non-porous material.

7. The prosthesis according to claim 1, wherein a distal portion of the material portion is free of the adhesive portion.

8. The prosthesis according to claim 1, wherein a distal portion of the material portion comprises the adhesive portion.

9. The prosthesis according to claim 1, wherein the adhesive portion is provided on an outer surface of the material portion in a pattern.

10. The prosthesis according to claim 1, wherein the liquid impermeable layer comprises a material having a thickness in the range of about 0.01 mm to about 0.5 mm.

11. The prosthesis according to claim 1, wherein the material portion comprises a material selected from the group consisting of elastomers, thermoplastics, fluoropolymers, polymer weaves, non-woven polymers, biodegradable polymers and biological material.

12. The prosthesis according to claim 11, wherein the material portion comprises a non-woven polymer.

13. The prosthesis according to claim 1, wherein the adhesive portion comprises an adhesive selected from the group consisting of carbomers, polycarbophil, cyanoacrylates, mussel adhesive protein derivatives, polyacrylic acid, polyethylene glycol, polyvinylpyrrolidone, epoxies, thermoset adhesives, UV adhesives, redux adhesives and natural adhesives.

14. The prosthesis according to claim 1, wherein the material portion is free from connection to a support structure.

15. The prosthesis according to claim 1, wherein the adhesive portion comprises an adhesive selected from the group consisting of carbomers, polycarbophil, mussel adhesive protein derivatives, polyacrylic acid, polyethylene glycol, polyvinylpyrrolidone, and natural adhesives.

16. A method of securing a prosthesis at a treatment site in a bodily lumen to inhibit migration of the prosthesis, the method comprising:

positioning a material portion of a prosthesis within the bodily lumen, the material portion including a liquid-impermeable material layer having a proximal opening, a distal opening and a wall extending between the proximal and distal openings, the wall being free from fluid flow through the wall between the proximal opening and the distal opening, a porous material layer having a pore size adapted for promoting tissue ingrowth; and contacting the porous material layer with the bodily lumen and adhering the portion of the material portion to the bodily lumen with an adhesive portion on the porous material layer so that the adhesive portion secures the porous material layer to the bodily lumen for at least 24 hours following implantation of the prosthesis at the site and the porous material layer is between the bodily lumen and the liquid-impermeable layer.

17. The method according to claim 16, further comprising expanding a body operably connected to the material portion so that the body provides a radial force against the bodily lumen.

18. The method according to claim 16, comprising positioning the prosthesis in the lower esophageal sphincter.

19. The method according to claim 16, comprising positioning the prosthesis in the duodenum.

* * * * *